United States Patent [19]

Russell et al.

[11] Patent Number: 5,252,753

[45] Date of Patent: Oct. 12, 1993

[54] PROCESS FOR THE PREPARATION OF CERTAIN SUBSTITUTED BIPHENYL TETRAZOLES AND COMPOUNDS THEREOF

[75] Inventors: Ronald Russell, Titusville; William V. Murray, Belle Mead, both of N.J.

[73] Assignee: Ortho Pharmaceutical Corporation, Raritan, N.J.

[21] Appl. No.: 786,666

[22] Filed: Nov. 1, 1991

[51] Int. Cl.$^5$ .................................... C07D 257/04
[52] U.S. Cl. ................................ 548/252; 548/250; 548/110
[58] Field of Search .................... 548/250, 110, 252

Primary Examiner—David B. Springer
Attorney, Agent, or Firm—Ralph R. Palo

[57] ABSTRACT

A process for producing a compound of formula I:

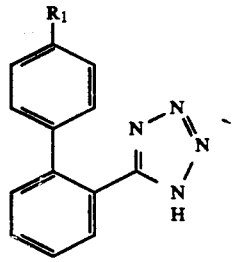

comprising reacting 5-(2-fluorophenyl)-1H-tetrazole with a Grignard reagent to produce the desired product is disclosed. Novel compounds produced by this process for use as intermediates in making certain angiotension II antagonists are also disclosed.

8 Claims, No Drawings

PROCESS FOR THE PREPARATION OF CERTAIN SUBSTITUTED BIPHENYL TETRAZOLES AND COMPOUNDS THEREOF

BACKGROUND OF THE INVENTION

The renin-angiotensin system is one of the primary regulatory mechanisms for blood pressure in humans. Two drugs which act on the renin-angiotensin system are captopril and enalapril which are angiotensin converting enzyme (ACE) inhibitors. See Ondetti, M. et al., *Science* 1977, 196, 441; Ondetti, M. et al., *J. Med. Chem.* 1981, 24, 355 and Patchette, A. et al., *Nature*, 1980, 288, 280. A potentially more selective site for inhibition would be at the angiotensin II receptor as discussed by Duncia, J. et al., *J. Med. Chem.*, 1990, 33, 1312; Carini; D. et al., *J. Med. Chem.*, 1990, 33, 1330; Carini, D. and Duncia, J., Eur. Pat. Appl. 0253310 (Jan. 20, 1988); Johnson, A. et al., *Drug News and Perspectives*, 1990, 3, (6), 337; Chang, L., et al., European Patent Application No. 0412594A, (Jul. 23, 1990); Naka, T., et al., JP 200963 (filed Jul. 27, 1990) and Roberts, D. et al., GB 18402 (filed Aug. 10, 1990).

Most of the compounds reported recently as angiotension II receptor antagonists have the (2'-tetrazol-5-yl)biphenyl-4-yl)methyl moiety attached to a heterocycle (HET) represented by the following formula II:

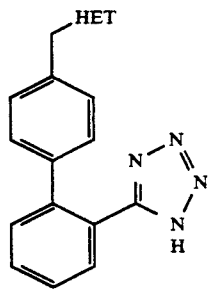

II

See Johnson, A., et al., *Drug News and Perspectives*, 1990, 3, (6), 337; Naka, T., et al., JP 200963 (filed Jul. 27, 1990); Roberts, D. et al., GB 18402 (filed Aug. 10, 1990). Chakravaty, P. K. et al, Eur. Pat. 0400974A (May 30, 1990); OKV, t, Setoi, H., Kayakiri, H., Inoue, I. and Kuroda, A., Eur. Pat. 0426021A (Oct., 26, 1990); Roberts, D. A., et al., Eur. Pat. 0425921A (May 18, 1990); Naka, T. and Nishikawa, K., Eur. Pat. 0425921A (Oct. 19, 1990) and Herold, P. and Bühlmayer, P., Eur. Pat. 0424317A (Oct. 10, 1990).

The preparation of compounds of the formula II starts with the intermediate 5-(4'-methyl[1,1'-biphenyl]-2-yl)-1H-tetrazole of the formula III:

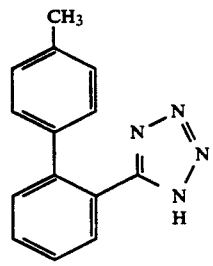

III which is prepared from the nitrile of the formula IV:

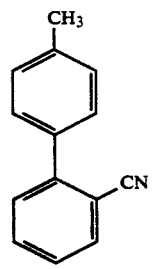

IV

The conversion of the compound of formula IV to the compound of formula III is a process which requires the use of either highly toxic tin reagents (e.g. $Bu_3SnN_3$) or the production of triphenylphosphine oxide and acrylonitrile. See, Aldrich, P. E., et al., U.S. Pat. No. 4,870,186 (Nov. 23, 1988); Aldrich, P. E., et al., U.S. Pat. No. 4,874,867 (Nov. 23, 1988); Aldrich, P. E., et al., Eur. Pat. 0291969 (May 19, 1988); Chakravarty, P. K., et al., Eur. Pat. 0401030A (May 31, 1990); Duncia, J. V., Pierce, M. E. and Santella, J. B. III, *J. Org. Chem.*, 1991, 56, 2395; George, E. F. and Riddell, W. D., U.S. Pat. No. 3,865,570 (Feb. 13, 1973) and Herbst, R. M. and Wilson, K. R., *J. Org. Chem.*, 1957, 22, 1142.

The preparation of certain biphenyl compounds has been reported when one reacts a Grignard reagent with a fluorobenzene which has a bis-oxazoline moiety. See, Cram, D. J., Katz, H. E. and Dicker, I. B., *J. Am. Chem. Soc.*, 1984, 106, 4987 and Meyers, A. I. and Williams, B. E., *Tetrahedron Lett.*, 1978, 223. Such compounds are, however, quite different from the compounds of formula III and those of the present invention.

It is an object of the present invention to develop a process for the preparation of compounds of the type represented by formula III which avoid the use or generation of highly toxic materials.

SUMMARY OF THE INVENTION

Accordingly, the present invention is directed to a process for the production of compounds of formula I:

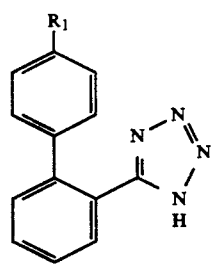

I wherein $R_1$ is defined hereafter, generally comprising reacting 5-(2-fluorophenyl)-1H-tetrazole with a Grignard reagent to produce the desired compound of formula I. The process produces the desired compound in a yield of about 72–82% without the use or generation of highly toxic materials. The process of the present invention also produces certain novel compounds.

DETAILED DESCRIPTION OF THE INVENTION

More particularly, the process of the present invention comprises producing certain biphenyl tetrazoles of formula I by the following reaction scheme:

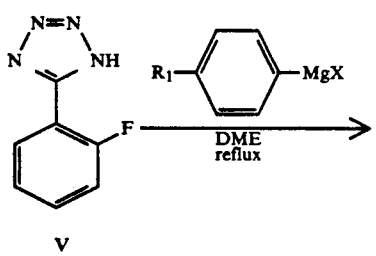

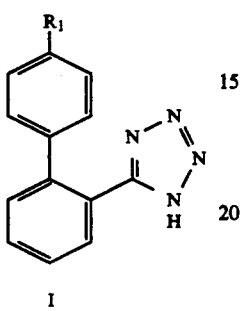

I wherein $R_1$ is any of $CH(OR_2)_2$, $CH_2OR_2$, $CH_2N[Si(R_2)_3]_2$, $CH=C(R_2)_2$, $C\equiv CR_2$, $C_1-C_4$ alkyl,

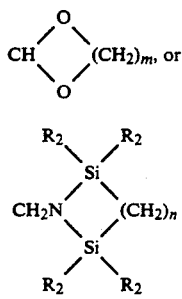

wherein $R_2$ is $C_1-C_3$ alkyl, n is 1–3, m is 2–4 and wherein X is Cl, Br or I.

In this process, a tetrazole of the formula V is treated with an excess of a Grignard reagent of the following formula:

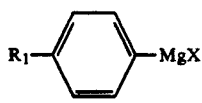

in a solvent such as diethylether, dimethoxyethane or dioxane and warmed to reflux, preferably for about 6 to 24 hours.

When $R_1$ is $C_1-C_4$ alkyl the Grignard reagent is either purchased from commercial sources (e.g. Aldrich Chemical Company, Inc.) or prepared by literature methods such as those described by DePuy, C. H. and R. A. Klein in *Organic Synthesis*, Coll. Vol V, Baumgarten, H. E., ed.; John Wiley and Sons: New York, 1973, pp 1058–1060 or Murray, W. V., Hadden, S. K. and Wachter, M. P., *J. Heterocycl. Chem.*, 1990, 27, 1933. The preparation of the protected aldehydes [see e.g.: a) Shauler, A. J. and Darley, P. A. *Chem. Rev.* 1967, 67, 427–440; b) Cole, J. E. et al., *J. Chem. Soc.*, 1962, 244; and c) Dann, A. E., et al., *J. Chem. Soc.*, Perkin Trans. I, 1979, 158] wherein $R_1$ is $CH(OR_2)_2$ and

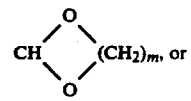

the protected benzyl alcohols (see e.g. Stork, G. and Takahashi, T., *J. Amer. Chem. Soc*, 1977, 99, 1275 or Auerbach, J. and Weinreb, S. M., *J. Chem. Soc.*, Chem. Commun., 1974, 298) wherein $R_1$ is $CH_2OR_2$, and the protected benzyl amines [see e.g. a) Pratt, J. R., Massey, W. D., Pinkerton, F. H. and Thames, S. F., *J. Org. Chem*; 1975, 40, 1090; b) Basha, F. Z. and DeBernardis, J. F., *Tetrahedron Lett.*, 1984, 25, 5271; and c) Diuric, S., Venit, J. and Magnus, P., *Tetrahedron Lett.*, 1981, 1787] wherein $R_1$ is $CH_2N[Si(R_2)_3]_2$ and

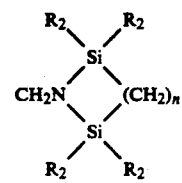

may be effected by techniques well known in the art from commercially (e.g. Aldrich Chemical Company, Inc.) available 4-bromobenzaldehyde, 4-bromobenzyl alcohol and 4-bromobenzyl amine, respectively. The preparation of the 4-bromophenylacetylenes wherein $R_1$ is $C\equiv CMe$ can be accomplished by the procedure of Hamer and Magee, *J. Chem. Soc.*, 1964, 1847 and wherein $R_1$ is $CH=C(R_2)_2$ can be accomplished by the procedure of Mirviss, S. R., *J. Org. Chem.*, 1989, 54, 1948.

The halogen X of the Grignard is chlorine, bromine or iodine and is determined by the choice of starting material for the Grignard preparation (i.e. 4-chlorotoluene gives $X=Cl$ ($R_1=CH_3$), 4-bromotoluene gives $X=Br$ ($R_1=CH_3$).

The tetrazole of the formula V may be prepared by techniques well known in the art as described in Herbst, R. M. and Wilson, K. R., *J. Org. Chem.*, 1957, 22, 1142. The preparation generally comprises reacting 2-fluorobenzonitrile with $NaN_3$ and glacial $CH_3COOH$ in the presence of a solvent such as n-butanol.

In the process of the present invention, after warming to reflux, the final product is obtained by techniques known in the art, including extraction with a suitable agent such as $CH_2Cl_2$, filtration and either crystallization or purification by column chromatography. The process produces product in yields of from about 72 to 82%.

A particularly preferred process according to the present invention comprises the production of compounds of the formula I wherein $R_1$ is $CH_3$.

Certain of the compounds produced by the process of the present invention are novel compounds. These compounds are compounds of formula I wherein $R_1$ is any of $CH(OR_2)_2$, $CH_2OR_2$, $CH_2N[Si(R_2)_3]_2$, $CH=C(R_2)_2$, $C\equiv CR_2$, $C_2-C_4$ alkyl. Each of these compounds and the other known compounds represented by formula I may be employed in the preparation of angiotension II receptor antagonists which have the (2'-tetrazol-5-yl)biphenyl-4-yl)methyl moiety attached to a heterocycle as described in greater detail in the Background of the Invention.

The process of the present invention will now be illustrated by the following Example, which is not intended and should not be considered a limitation to the present invention.

EXAMPLE

Preparation of 5-(4'-methyl[1,1'-biphenyl]-2-yl)-1H-tetrazole

A 4-necked 3 l round-bottom flask was charged with 5-(2-fluorophenyl)-1H-tetrazole (32.8 g, 0.2 mol) and dry DME (1300 ml) under nitrogen. To this ice-cold solution was slowly added a 1M solution of p-tolylmagnesium bromide in diethyl ether (600 ml, 0.6 mol). After the addition had been completed, the diethyl ether was removed by simple distillation and the resulting DME solution was warmed to reflux for 16 h under nitrogen. With ice-bath cooling, the reaction mixture was slowly quenched with 6N HCl (130 ml). The DME was removed under reduced pressure and the resulting aqueous residue was extracted with $CH_2Cl_2$. The combined $CH_2Cl_2$ extracts were washed with 2N NaOH (3×100 ml) and these combined extracts were acidified to a pH of 1 with concentrated HCl. The acidic aqueous phase was extracted with $CH_2Cl_2$ and these combined extracts were washed with brine and dried ($Na_2SO_4$). Solvent removal under vacuum produced 46.2 g of tan material which was purified by crystallization from EtOAc/hexane (2/1, total volume=250 ml). The compound of formula III was obtained (32.4 g, 68.6%) as a tan solid, mp 141°-146° C. [lit. mp 152°-154° C. (toluene); Chakravarty, P. K., et al., Eur. Pat. 0401030 (May 31, 1990)]. The filtrate was purified by silica gel filtration with $CH_2Cl_2$/MeOH/AcOH (97.5/2.70/0.05) and then crystallized from the above solvent mixture to produce another 4.54 g (9.6%) of the compound of formula III, mp 146°-148° C. An analytical sample was prepared by recrystallization from toluene (2×) to afford a tan solid, mp 144°-148° C.

Anal. Calc'd for $C_{14}H_{12}N_4$: C, 71.17; H, 5.12; N, 23.71. Found: C, 71.16; H, 5.10; N, 24.08.

The 5-(2-fluorophenyl)-1H-tetrazole starting material was prepared as follows. A 3-necked 500 ml round-bottom flask was charged with 2-fluorobenzonitrile (48.4 g, 0.4 mol), n-butanol (160 ml), $NaN_3$ (34.3 g, 0.528 mol) and glacial acetic acid (31.7 g, 0.528 mol). The mixture was warmed to a mild reflux for 24 h under nitrogen behind a safety shield. After the mixture had cooled to room temperature, it was again charged with $NaN_3$ (34.3 g, 0.528 mol) and glacial acetic acid (31.7 g, 0.528 mol). The mixture was warmed to a mild reflux for an additional 24 h under nitrogen, cooled and then diluted with diethyl ether (320 ml). This organic mixture was extracted with 2N NaOH (4×100 ml) and the combined ice-cold basic extracts were carefully acidified to pH 1 with concentrated hydrochloric acid. The product was isolated as a light gray solid (45.2 g, 68.9%) after drying under vacuum at 60° C., mp 160.5°-162° C. [lit. mp 160°-162° C.; George, E. F. and Riddell, W. D., U.S. Pat. No. 3,865,570 (Feb. 13, 1973)]. There was obtained a second crop of product (1.0 g, 1.5%). A 1.0 g sample of this material was crystallized from water to produce a white solid, mp 162.5°-163.5° C.

Anal. Calc'd for $C_7H_5FN_4$: C, 51.22; H, 3.07; N, 34.13. Found: C, 51.35; H, 3.02; N, 34.43.

What is claimed is:

1. A process for the preparation of a compound of the formula I:

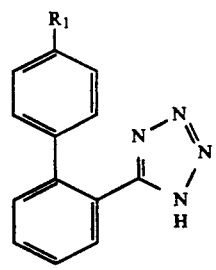

wherein $R_1$ is any of $CH(OR_2)_2$, $CH_2OR_2$, $CH_2N[Si(R_2)_3]_2$, $CH-C(R_2)_2$, $C=CR_2$, $C_1-C_4$ alkyl,

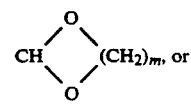

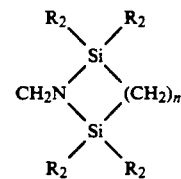

comprising reacting a compound of the formula V:

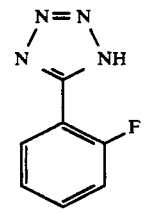

with a reagent of the formula:

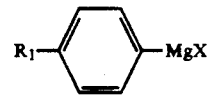

wherein X is any of Cl, Br or I, thereby producing the compound of formula I.

2. The process of claim 1, wherein the reaction is carried out in the presence of a solvent.

3. The process of claim 2, wherein the solvent is dimethoxyethane.

4. The process of claim 1, wherein the reaction is carried out by heating to reflux.

5. The process of claim 1, wherein $R_1$ is $CH_3$.

6. A compound of the formula I:

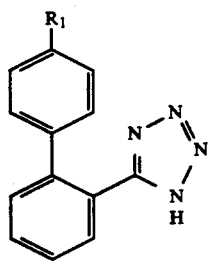
wherein R₁ is any of $CH(OR_2)_2$, $CH_2OR_2$, $CH_2N[Si(R_2)_3]_2$, $CH=C(R_2)_2$, $C\equiv CR_2$,
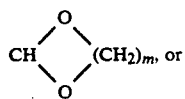 or
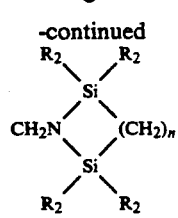
wherein $R_2$ is $C_1$–$C_3$ alkyl, n is 1–3 and m is 2–4.
7. The compound of claim 6, wherein R₁ is
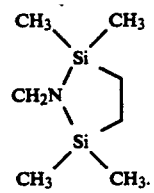
8. The compound of claim 6, wherein R₁ is
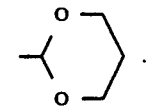
* * * * *